US005912194A

United States Patent [19]

Everhart et al.

[11] Patent Number: 5,912,194

[45] **Date of Patent: *Jun. 15, 1999**

[54] PERMEABLE LIQUID FLOW CONTROL MATERIAL

[75] Inventors: Dennis Stein Everhart, Alpharetta; Elizabeth Deibler Gadsby, Marietta; Kristi Lynn Kiick-Fischer; Roger Bradshaw Quincy, III, both of Alpharetta, all of Ga.; Alice Yvonne Romans-Hess, Fremont; Garry Roland Woltman, Neenah, both of Wis.

[73] Assignee: Kimberly Clark Corp., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/706,111

[22] Filed: Aug. 30, 1996

[51] Int. Cl.[6] .............................. B32B 7/02; B32B 5/16; B05D 1/12

[52] U.S. Cl. .......................... 442/118; 428/221; 428/339; 428/474.4; 428/480; 428/522; 427/180; 427/256; 427/384; 427/414

[58] Field of Search ............................. 428/221, 98, 339, 428/474.4, 480, 522; 427/180, 256, 384, 414, 430.1; 442/118

[56] References Cited

U.S. PATENT DOCUMENTS

| | | | |
|---|---|---|---|
| 2,262,770 | 11/1941 | La Piana | 260/6 |
| 2,262,771 | 11/1941 | La Piana | 260/6 |
| 2,310,795 | 2/1943 | La Piana et al. | 106/146 |
| 2,453,752 | 11/1948 | La Piana et al. | 260/6 |
| 2,979,422 | 4/1961 | Bersin et al. | 117/106 |
| 3,104,154 | 9/1963 | Morimoto et al. | 18/54 |
| 3,188,233 | 6/1965 | Powers et al. | 117/140 |
| 3,202,748 | 8/1965 | Naka et al. | 264/194 |
| 3,494,775 | 2/1970 | Coscia et al. | 106/124 |
| 3,690,925 | 9/1972 | Morris | 455/41 |
| 4,309,247 | 1/1982 | Hou et al. | 162/149 |
| 4,523,995 | 6/1985 | Pall et al. | 210/504 |
| 4,761,161 | 8/1988 | Potschke | 8/543 |
| 4,859,340 | 8/1989 | Hou et al. | 210/502.1 |
| 4,981,591 | 1/1991 | Ostreicher | 210/502.1 |
| 5,055,316 | 10/1991 | Hoffman et al. | 427/2.13 |
| 5,085,784 | 2/1992 | Ostreicher | 210/767 |
| 5,208,075 | 5/1993 | Kroner et al. | 427/389.9 |
| 5,229,172 | 7/1993 | Cahalan et al. | 427/536 |
| 5,260,396 | 11/1993 | Kroner et al. | 527/201 |
| 5,494,744 | 2/1996 | Everhart et al. | 428/337 |

FOREIGN PATENT DOCUMENTS

| | | |
|---|---|---|
| 538901 | 4/1957 | Canada . |
| 0199171 | 10/1986 | European Pat. Off. . |
| 2364524 | 7/1974 | Germany . |
| 3536318 A1 | 4/1987 | Germany . |
| 4108170 | 9/1992 | Germany . |
| 42-16065 | 9/1967 | Japan . |
| 45-34390 | 11/1970 | Japan . |
| 45-34391 | 11/1970 | Japan . |
| 40-48590 | 12/1974 | Japan . |
| 71-70904 | 10/1982 | Japan . |
| 425689 | 3/1935 | United Kingdom . |
| 97/15710 | 5/1997 | WIPO . |

OTHER PUBLICATIONS

Theodore H. Meltzer, *Filtration in the Pharmaceutical Industry*, Marcel Dekker, Inc., New York, 1987, pp. 310–314.

Zaverio M. Ruggeri, Mechanisms of Shear–induced Platelet Adhesion and Aggregation, *Thrombosis and Haemostasis–Journal of the International Society of Thrombosis and Haemostasis*, Jul. 1, 1993, Schattauer Stuttgart, New York, 1993, pp. 119–123.

Erik Kissa and Robert H. Dettre: "*Sorption of Surfactants in Polyester Fibers*", Textile Research Journal, vol. 45, No. 11, Nov. 1975, US, pp. 773–777, XP002047830.

N. Gomez, M.R. Julia, I. Munoz, M.R. Infante, A. Pinazo, A. Naik and P. Erra: "*Wool Treatments with Mixtures of Sulphite and Amphiphilic Cationic Protein Hydrolysate*", Journal Of The Textile Institute, vol. 85, No. 2, 1994, Manchester, Great Britain, pp. 215–224, XP002047829.

*Primary Examiner*—Ponnathapura Achutamurthy
*Assistant Examiner*—P. Ponnaluri
*Attorney, Agent, or Firm*—Karl V. Sidor

[57] ABSTRACT

A permeable, liquid flow control material composed of: 1) a permeable sheet having a plurality of individual exposed surfaces, at least a portion of which have a surface energy of less than about 45 dynes/cm; and 2) amphiphilic proteins adsorbed onto at least some individual exposed surfaces to define a gradient distribution of amphiphilic protein coating along at least one dimension of the permeable sheet so that the adsorbed amphiphilic protein coating provides controlled wettability along at least one dimension of the liquid flow control material. Desirably, the liquid flow control material is substantially free of fugitive amphiphilic proteins. The material may be used as a permeable, bodyside cover material for absorbent personal care products.

25 Claims, 10 Drawing Sheets

PERMEABLE LIQUID FLOW CONTROL MATERIAL

FIELD OF THE INVENTION

This invention relates to permeable materials that are wettable.

BACKGROUND OF THE INVENTION

Sheets of apertured films, woven fabrics and nonwoven materials are widely used in many types of products such as, for example, personal care products, garments, medical fabrics and the like. Some sheets made from certain inexpensive raw materials could have an even wider range of applications in these products if the sheets could be designed to have enhanced properties or attributes.

For example, polyolefins are widely used in the manufacture of sheets of apertured films, woven fabrics, and nonwoven materials. Many types of polyolefin sheets tend to be hydrophobic and relatively inert. That is, the low surface free energy of polyolefins (e.g., polypropylene) and their relatively chemically inert nature render many unmodified polyolefins ill-suited for providing attributes other than those based on hydrophobic interactions.

In the past, chemical coatings and/or internal additives have been added to sheets of materials to impart desired properties. Many of these coatings and/or additives present problems related to cost, effectiveness, durability and/or the environment. These coatings generally provide a uniform wettability or hydrophilicity across one or more dimensions of the sheets of materials. Sheet materials having substantially uniform wettability across their thickness or Z-direction may retain or hold significant amounts of liquid in the cover material instead of releasing the liquid to an absorbent core. This may be particularly noticeable if the liquid is colored or viscous in nature such as, for example, blood or menses. Thus, there is still a need for a permeable material having controlled, non-uniform wettability so that it can be used to direct the transfer or flow of liquid through the material. There is also a need for a permeable, bodyside cover material for use in an absorbent personal care product. There is also a need for a permeable, bodyside cover material for use in an absorbent personal care product which provides non-uniform wettability along at least one dimension of the cover material. This need extends to a permeable, bodyside cover material (for an absorbent personal care product) coated with a readily available, inexpensive, natural, renewable and non-toxic material that can provide non-uniform wettability to a relatively hydrophobic substrate. Meeting these needs is important since it is both economically and environmentally desirable to substitute relatively complex chemical surface modification of inexpensive (and often recyclable) substrates with inexpensive, readily available natural materials.

DEFINITIONS

As used herein, the term "amphiphilic protein" refers to proteins having both hydrophobic regions and hydrophilic regions. For example, amphiphilic proteins may be selected from classes of globular and/or random coil proteins. As another example, amphiphilic proteins may be milk proteins. As a further example, amphiphilic proteins may include proteins such as those found in bovine milk including, but not limited to, various caseins and whey proteins.

As used herein, the term "relatively low surface energy" refers to surface energies (i.e., surface free energies) attributed to materials that are not generally considered to be water wettable. Generally speaking, such materials have a surface energy of less than about 45 dynes per centimeter (dynes/cm) as determined in accordance with critical surface tension of wetting techniques described by Bennet, M. K. and Zisman, W. A.; *Relation of Wettability by Aqueous Solutions to the Surface Constitution of Low Energy Solids*; J. Phys. Chem., pps. 1241–1246, Volume 63 (1959). Many such materials have a surface energy ranging from about 29 to about 35 dynes/cm.

As used herein, the term "relatively high surface tension" refers to a level of attractive force in a liquid exerted by the molecules below the surface upon those at the surface/air interface, resulting from the high molar concentration of a liquid compared to the low molar concentration of a gas. Relatively high surface tensions are characteristic of, for example, some aqueous liquids and/or aqueous solutions having little or no added surfactants or other agents that reduce the surface tension. Surface tension may be determined from measurements of the contact angle of sessile drops using a goniometer such as, for example goniometer model No. 100-00 115 (equipped with videocamera) available from Rame-Hart, Inc., or by methods such as, for example, DuNouy ring methods. Relatively high surface tension for the purposes of the present invention is a surface tension of at least about 45 dynes/cm. Desirably, the surface tension is greater than 45 dynes/cm.

As used herein, the term "shear stress conditions" refers to conditions under which a shearing stress (force per unit area) is applied to a liquid. As an example, for a given volume of a liquid, increasing the rate at which the liquid penetrates or passes through a relatively permeable sheet such as, for example, a polyolefin nonwoven fibrous web (i.e., by decreasing the residence or exposure time) results in an increased shear stress at the fiber/liquid interface. Generally speaking, shear stress applied to the liquid may be transferred or applied to amphiphilic macromolecules that may be present in the liquid. In addition to shear stress conditions, residence time or dwell time may also need to be sufficient for the amphiphilic macromolecule to interact with the surface of a substrate (e.g., permeable sheet). Residence time may be influenced by the thickness and/or basis weight of a permeable sheet. A relatively long residence time may generally indicate little or no shear stresses and a relatively short residence time may generally indicate shear stress conditions. Shear stress conditions may occur in liquid flow having generally laminar or turbulent flow characteristics.

As used herein, the term "adsorbed" refers to a type of adhesion which takes place at the surface of a solid in contact with another medium (e.g., a liquid), resulting in the accumulation or increased concentration of molecules from that medium in the immediate vicinity of the surface.

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing, spunbonding, wet-forming and various bonded carded web processes.

As used herein, the term "spunbonded web" refers to a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563.

As used herein, the term "meltblown fibers" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly dispersed meltblown fibers. The meltblown process is well-known and is described in various 35 patents and publications, including NRL Report 4364, "Manufacture of Super-Fine Organic Fibers" by V. A. Wendt, E. L. Boone, and C. D. Fluharty; NRL Report 5265, "An Improved Device or the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al. As used herein, the term "microfibers" means small diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers may be found in, for example, U.S. Pat. No. 5,213,881, entitled "A Nonwoven Web With Improved Barrier Properties".

As used herein, the term "apertured film-like material" refers to a generally flat or planar layer of material which has been punched, drilled, apertured, stretched, perforated, embossed, patterned, crinkled and/or otherwise processed so that it may have relatively gross or visible openings with or without a pattern or texture in the thickness dimension (i.e., Z-direction) of the material. Exemplary apertured film-like materials include, but are not limited to, perf-embossed films, textured apertured films, reticulated apertured films, contoured apertured films, film-nonwoven apertured laminates, and expanded plexi-filamentary films.

As used herein, the term "sheet" refers to a material that can be a woven fabric, knit fabric, nonwoven fabric or film-like material (e.g., an apertured film-like material).

As used herein, the term "solution" refers to any relatively uniformly dispersed mixture of one or more substances (e.g., solute) in one or more other substances (e.g., solvent). Generally speaking, the solvent may be a liquid such as, for example, water and/or mixtures of liquids. The solvent may contain additives such as salts, acids, bases, viscosity modifiers, preservatives, disinfectants, anti-microbial agents and the like. The solute may be any material adapted to uniformly disperse in the solvent at the appropriate level, (e.g., ionic level, molecular level, colloidal particle level or as a suspended solid) . For example, a solution may be a uniformly dispersed mixture of ions, of molecules, of colloidal particles, or may even include mechanical suspensions.

As used herein, the terms "permeable" and "permeability" refer to the ability of a fluid, such as, for example, a gas to pass through a particular porous material. Permeability may be expressed in units of volume per unit time per unit area, for example, (cubic feet per minute) per square foot of material (e.g., ($ft^3$/minute/$ft^2$)). Permeability may be determined utilizing a Frazier Air Permeability Tester available from the Frazier Precision Instrument Company and measured in accordance with Federal Test Method 5450, Standard No. 191A, except that the sample size was 8"×8" instead of 7"×7". Although permeability is generally expressed as the ability of air or other gas to pass through a permeable sheet, sufficient levels of gas permeability may correspond to levels of liquid permeability to enable the practice of the present invention. For example, a sufficient level of gas permeability may allow an adequate level of liquid to pass through a permeable sheet with or without assistance of a driving force such as, for example, an applied vacuum or applied gas pressure. Generally speaking, a permeable sheet may have a permeability of at least about 20 cubic feet per minute per square foot (cfm/$ft^2$), as measured for a substantially dry sheet prior to processing. It is contemplated that a sheet having a permeability of less than about 20 cfm/$ft^2$, as measured for a substantially dry sheet prior to processing, could be used successfully in the practice of the present invention with (or in some cases without) assistance of a driving force such as, for example, an applied vacuum or applied gas pressure. As an example, a permeable sheet may have permeability of from about 25 to over 200 cfm/$ft^2$, as measured or a substantially dry sheet prior to processing. As another example, a permeable sheet may have a permeability of from about 35 to about 150 cfm/$ft^2$, as measured for a substantially dry sheet prior to processing.

As used herein, the term "superabsorbent" refers to absorbent materials capable of absorbing at least 10 grams of aqueous liquid (e.g. water, saline solution or synthetic urine Item No. K-C 399105 available from PPG Industries) per gram of absorbent material while immersed in the liquid for 4 hours and holding the absorbed liquid while under a compression force of up to about 1.5 pounds per square inch.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates or materials added to enhance processability of a composition.

SUMMARY OF THE INVENTION

The problems described above are addressed by the present invention which is directed to a permeable, liquid flow control material composed of: 1) a permeable sheet having a plurality of individual exposed surfaces, at least a portion of which have a surface energy of less than about 45 dynes/cm; and 2) amphiphilic proteins adsorbed onto at least some individual exposed surfaces to define a gradient distribution of amphiphilic protein coating along at least one dimension of the permeable sheet so that the adsorbed amphiphilic protein coating provides controlled wettability along at least one dimension of the liquid flow control material. Desirably, the liquid flow control material is substantially free of fugitive amphiphilic proteins. That is, the amphiphilic proteins adsorbed to the permeable sheet are substantive to water wash and other aqueous solution washes.

The amphiphilic proteins may be adsorbed onto at least some individual exposed surfaces thereby defining a patterned protein coating on the permeable sheet. The coating of amphiphilic proteins may be uniformly adsorbed onto individual exposed surfaces but in only discrete portions of the sheet material.

Generally speaking, the amphiphilic proteins may be selected from the group consisting of globular proteins and random coil proteins. The amphiphilic protein-coated sheet desirably has a critical surface tension of wetting greater than about 50 dynes per centimeter. For example, the amphiphilic protein-coated sheet may have a critical surface tension of wetting greater than about 60 dynes per centimeter.

In an aspect of the invention, the liquid flow control material may have a liquid retention of less than about 3.5 percent, by weight. For example, the material may have a liquid retention of less than about 2 percent, by weight. In another aspect of the invention, the liquid flow control material may have a liquid retention of greater than about 3.5 percent, by weight, when surface or side of the material having the lower surface tension of wetting is the surface or side which first contacts the liquid. For example, the liquid flow control material may have a liquid retention of up to about 5 percent, by weight, and provide a relatively stain-free and/or relatively dry surface when surface or side of the material having the lower surface tension of wetting is the surface or side which first contacts the liquid.

The liquid flow control material may have a gradient distribution of amphiphilic protein coating along at least two dimensions of the permeable sheet. Accordingly, the adsorbed amphiphilic protein coating may provide controlled wettability along at least two dimensions of the permeable sheet.

According to the invention, the permeable sheet may be a matrix of fibrous material. For example, the permeable sheet may be selected from nonwoven webs of meltblown fibers, nonwoven webs of continuous spunbond filaments and bonded carded webs. The nonwoven web of meltblown fibers may include one or more secondary materials selected from the group consisting of textile fibers, wood pulp fibers, particulates and super-absorbent materials. In an embodiment of the invention, at least a portion of the fibrous material is a bi-component material selected from bi-component fibers and bi-component filaments. In another embodiment, the permeable sheet may be an apertured, film-like material.

Generally speaking, the permeable, liquid flow control material may be used in applications where it is desirable to direct the flow, passage or distribution of a liquid within or through a permeable material. The material may be included in products such as, for example, surgical pads, bed pads, liquid applicator devices and the like. The material may be used as a liquid intake material, liquid distribution material, or liquid retention material in the products described above as well as in absorbent personal care products.

According to the invention, the permeable, liquid flow control material may be in the form of a permeable, bodyside cover material for absorbent personal care products. Such cover materials may be used in personal care products including, but not limited to, feminine care products, diapers, training pants, adult incontinence products and the like.

In an embodiment of the invention, the permeable, liquid flow control material may utilize amphiphilic macromolecules as the material adsorbed on at least some individual exposed surfaces of the permeable sheet. Such amphiphilic macromolecues may include, but are not limited to, synthetic polymers such as ionomers with separated areas of ionicity in an otherwise hydrophobic polymer, multiblock copolymers where every other block is highly charged or polar with the intervening blocks uncharged or nonpolar, protein,fatty acids, glycoproteins, and other biological macromolecules with separated areas of hydrophilicity and hydrophobicity.

BRIEF DESCRIPTION OF THE DRAWINGS

FIG. 1 is a micrograph of an exemplary protein-coated permeable sheet.

FIGS. 5A and 5B are photographs of an absorbent personal care product and permeable cover material.

DETAILED DESCRIPTION OF THE INVENTION

Figure 2:
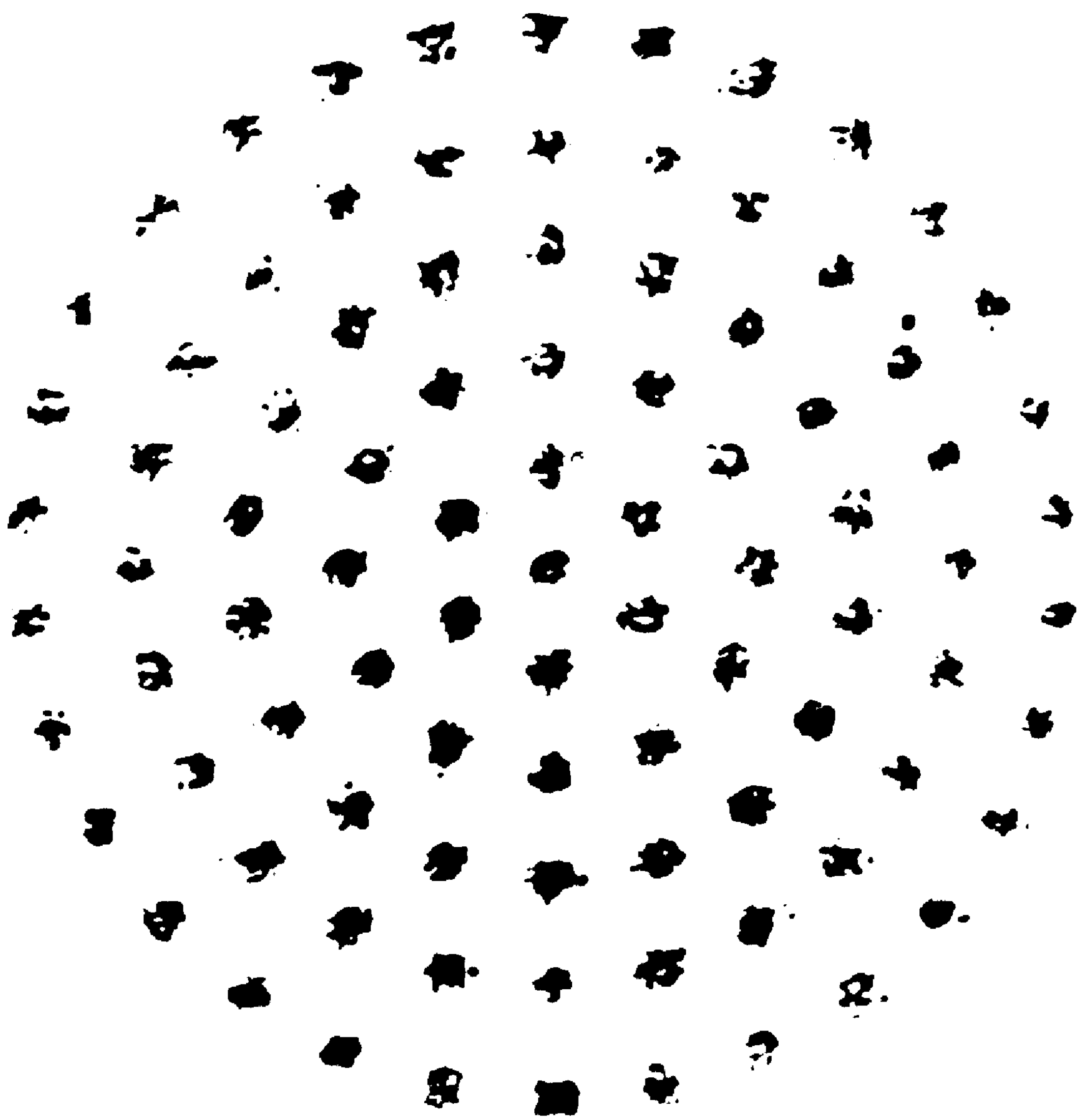
FIG. 2 is a representation of a stained, vacuum extracted, exemplary protein-coated permeable sheet.

An exemplary method of applying a protein coating to a substrate is described in U.S. Pat. No. 5,494,744 to Everhart et al., issued on Feb. 27, 1996, the contents of which is incorporated by reference. Such a method may be employed to apply an amphiphilic macromolecule (e.g., amphiphilic protein) coating to a substrate to manufacture a permeable, liquid flow control material. Such a method may also be used to manufacture a permeable, bodyside cover material for absorbent personal care products. Such cover materials may be used in personal care products including, but not limited to, feminine care products, diapers, training pants, adult incontinence products and the like.

Generally speaking, the method includes the steps of coating individual exposed surfaces of a permeable material (e.g., a matrix of fibrous material or an apertured film-like material) with amphiphilic macromolecules (e.g., amphiphihlic proteins).

The permeable sheet may be unwound from a supply roll or may be formed by one or more sheet making processes and passed directly into the coating process. Exemplary sheet-making processes include processes such as meltblowing processes, spunbonding processes, bonded-carded web-making processes, wet-laying processes, apertured film-forming processes, and the like. The permeable sheet may be passed through a pre-treatment station to modify the structure of the sheet. For example, the sheet may be calendered with a flat roll, point bonded or pattern bonded roll and/or aperturing roll in order to achieve desired strength, functional and/or textural properties.

Although it is not necessary for the successful deposition of the amphiphilic macromolecule (e.g., amphiphilic protein) coating on the permeable sheet in the practice of the present invention, it is contemplated that at least a portion of a surface of the sheet could be modified by various known surface modification techniques prior to entering the continuous process of coating individual exposed surfaces of the permeable sheet with amphiphilic macromolecules. Exemplary surface modification techniques include, for example, chemical etching, chemical oxidation, ion bombardment, plasma treatments, flame treatments, heat treatments, and/or corona discharge treatments.

The permeable sheet may be an apertured film-like material. For example, the apertured film-like material may be selected from perf-embossed films, textured apertured films, reticulated apertured films, contoured apertured films, film-nonwoven apertured laminates, and expanded plexi-filamentary films.

Alternatively and/or additionally the permeable sheet may be a matrix of fibrous material such as one or more woven fabrics, knit fabrics or nonwoven fabrics. That is, the permeable sheet may be either an apertured film-like material, a matrix of fibrous material or any suitable combination of the same. If the permeable sheet is a nonwoven fabric, it may be a nonwoven fibrous web such as, for example, a bonded carded web, spunbond web, web of meltblown fibers, fibrous batt, fibrous mat and/or multi-ply fibrous web containing the same type of fibrous web or a multi-ply fibrous web containing different types of fibrous webs. If the permeable sheet is a web of meltblown fibers, it may include meltblown microfibers. These nonwoven webs may be formed from thermoplastic polymers or thermoset polymers. If the nonwoven web is formed from a polyolefin, the polyolefin may be polyethylene, polypropylene, polybutene, ethylene copolymers, propylene copolymers and butene copolymers. The fibers and/or filaments may be formed from blends that contain various pigments, additives, strengthening agents, flow modifiers and the like. Such fabrics are described in U.S. Pat. Nos. 4,041,203, 4,374,888, and 4,753,843, the contents of which are incorporated herein by reference. Those patents are assigned to the Kimberly-Clark Corporation, the assignee of the present invention.

The permeable sheet may be a nonwoven web that may also be a composite material made of a mixture of two or more different fibers or a mixture of fibers and particulates. Such mixtures may be formed by adding fibers and/or particulates to the gas stream in which meltblown fibers are carried so that an intimate entangled commingling of meltblown fibers and other materials, e.g., wood pulp, staple fibers and particulates such as, for example, activated carbon, silica, and/or hydrocolloid (hydrogel) particulates commonly referred to as superabsorbent materials, occurs prior to collection of the meltblown fibers upon a collecting device to form a coherent web of randomly dispersed meltblown fibers and other materials such as disclosed in U.S. Pat. Nos. 4,100,324, and 5,350,624, the disclosure of which is hereby incorporated by reference.

If the permeable sheet is a nonwoven web, the fibrous material in the nonwoven web may be joined by interfiber bonding to form a coherent web structure. Interfiber bonding may be produced by entanglement between individual meltblown fibers, carded fibers, spunbond filaments and/or other fibrous materials. Some fiber entangling is inherent in the meltblown process, bonding-carding process and/or spunbond process but may be generated or increased by processes such as, for example, hydraulic entangling or needlepunching. Alternatively and/or additionally a bonding agent may be used to increase the desired bonding. If at least a portion of the fibrous material in the permeable sheet is cellulosic fibrous material, some interfiber bonding may be attributable to "paper" bonding.

The permeable sheet (either before or after processing) may have a basis weight ranging from about 6 gsm to about 400 gsm. For example, the permeable sheet may have a basis weight ranging from about 12 gsm to about 250 gsm. Desirably, the permeable sheet may have a basis weight ranging from about 17 gsm to about 102 gsm. It is contemplated that, after processing, any number of treated permeable sheets may be joined together or treated permeable sheets may be joined to other materials to form a consolidated material that may have a basis weight within the range of 6 gsm to 400 gsm or even greater (e.g., 400 gsm or more).

In order to apply an amphiphilic macromolecule coating, the permeable sheet passes under a means or device for providing a solution containing amphiphilic macromolecules. While the solution is typically an aqueous solution, it is contemplated that non-aqueous solutions may be used. Such non-aqueous solutions may contain one or more organic solvents. In some cases, it is contemplated that the organic solvents might affect the conformation of the amphiphilic macromolecules to enhance adsorption.

Generally speaking, the amphiphilic macromolecules may be amphiphilic proteins. The aqueous solution of amphiphilic macromolecules (e.g., amphiphilic proteins) should have a relatively high surface tension (i.e., the aqueous solution of amphiphilic macromolecules should have a surface tension of about 45 dynes/cm or greater). The means for providing an aqueous solution containing amphiphilic macromolecules distributes the aqueous solution substantially across and onto a first surface of the continuously advancing permeable sheet.

The means or device for depositing the aqueous solution containing amphiphilic macromolecules (e.g., amphiphilic proteins) deposits the amphiphilic macromolecules at conditions under which a shearing stress is applied to the aqueous solution. A description of such conditions may be found at, for example, U.S. Pat. No. 5,494,744, previously incorporated by reference.

The liquid depositing device may be composed of at least one liquid distribution element. For example, multiple liquid distribution elements may be arranged in series. The liquid distribution element may be a spillway adapted to produce a stream or shower of the aqueous solution of amphiphilic macromolecules (e.g., amphiphilic proteins) so that it is under shear stress conditions as it contacts the permeable sheet. The liquid distribution element may also be one or more nozzles and/or orifices which sprays, squirts, jets or otherwise conveys the aqueous solution so that it is under shear stress conditions as it contacts the permeable sheet. It is contemplated that the liquid distribution element may be composed of a reservoir of the aqueous solution of amphiphilic macromolecules (e.g., amphiphilic proteins) designed so that the permeable sheet passes over either an interior or exterior surface across one or more openings or orifices which provides contact with the aqueous solution of amphiphilic macromolecules (e.g., amphiphilic proteins) under shear stress conditions. It is also contemplated that the liquid distribution element may be a reservoir of the aqueous solution into which the permeable sheet passes at a rate of travel through the reservoir such that shear stress conditions are created at the interface between one or more surfaces of the permeable sheet and the aqueous solution.

The liquid distribution element may be composed of a reservoir and a spillway adapted to produce a relatively uniform distribution of the aqueous solution to produce a layer of liquid on top of the permeable sheet. A vacuum may be applied simultaneously with (and on the surface opposite to) the deposition of the aqueous solution to generate shear stress conditions in the aqueous solution as it passes through the permeable sheet. It is contemplated that application of vacuum may be delayed so that it is not simultaneous with the deposition of aqueous solution. Generally speaking, the vacuum level should be sufficient to draw the aqueous solution through the permeable sheet under shear stress conditions. As an example, the vacuum level may be greater than about 60 inches of water. As another example, the vacuum level may range from about 60 to about 270 or more inches of water. A description of an exemplary liquid distribution element may be found in U.S. Pat. No. 5,486,381, which is assigned to the assignee of the present application, the contents of which are incorporated by reference in their entirety.

As discussed above, the means for applying a vacuum to a second surface of the continuously advancing permeable sheet are located near the liquid deposition element. Generally speaking, the vacuum means may be composed of at least one vacuum element. Multiple vacuum elements may be arranged in series. The vacuum element may be a conventional vacuum channel or groove such as, for example, a vacuum slot. The vacuum means should be adapted to handle flow rates/volumes of aqueous solution generally corresponding to the flow rates/volumes out of the liquid deposition means.

The liquid deposition means and the vacuum means may be configured to deposit the aqueous solution on the permeable sheet in the general form of shapes, patterns, figures, alphanumeric characters, words, spots, pictures and the like. The vacuum means may contain a variety of configurations such as, for example, unevenly spaced vacuum slots or slits (or shaped openings) designed to produce a gradient deposition. It is contemplated that the liquid deposition means and the vacuum means could be configured to provide intermittent deposition of aqueous solution on the permeable sheet so that step-wise or unit-wise operation may be achieved.

Upon application of the vacuum to a second surface (opposite the first surface to which solution is initially contacted) of the permeable sheet, a substantial portion of the aqueous solution containing amphiphilic macromolecules (e.g., amphiphilic proteins) is drawn from the first surface and substantially through the permeable sheet. This passage of the aqueous solution through the permeable sheet is generally thought to generate the shear stress conditions necessary to provide appropriate levels of adsorption of amphiphilic macromolecules (e.g., amphiphilic proteins) onto the individual exposed surfaces of the permeable sheet.

Generally speaking, evacuation of the aqueous solution of amphiphilic macromolecules (e.g., amphiphilic proteins) under vacuum levels described above to achieve suitable shear stress conditions may be accomplished with a sheet having a permeability of at least about 20 cfm/ft$^2$, as measured for a substantially dry sheet prior to being processed. For example, the permeability of the sheet may range from about 50 to over 200 cfm/ft$^2$, as measured for a substantially dry sheet prior to being processed. If a sheet has inadequate permeability, the aqueous solution may puddle or pool on the first surface and may be non-uniformly concentrated, absorbed or diffused through the sheet. In such cases, it is generally thought that satisfactory conditions could be achieved by applying higher levels of vacuum, higher pressures and/or levels of force to the aqueous solution of amphiphilic macromolecules (e.g., amphiphilic proteins) contacting the permeable sheet and/or an applied gas pressure to drive the aqueous solution through the sheet thereby generating the appropriate sheer stress conditions.

According to the present invention, it may be desirable to wash or rinse the permeable sheet after being contacted with the aqueous solution of amphiphilic macromolecules (e.g., amphiphilic proteins). Washing or rinsing (not shown) the coated permeable sheet should be carried out using an aqueous liquid having a relatively high surface tension (e.g., water). Although the volume of the liquid wash or rinse may vary greatly, it has been found that a volume of liquid rinse generally similar to the volume of aqueous solution of amphiphilic proteins may be satisfactory (e.g., from about 0.5 to about 1.5 times the volume of amphiphilic macromolecule (e.g., amphiphilic protein) solution).

In general, the aqueous solution of amphiphilic macromolecules (e.g., amphiphilic proteins) should be able to flow freely. For example, the aqueous solution of amphiphilic macromolecules (e.g., amphiphilic proteins) may have a viscosity of from about 0.1 to about 5 centipoise. Lower viscosity solutions appear to be desirable. However, it is contemplated that more viscous aqueous solutions could be used in the practice of the present invention provided that appropriate shear stress conditions can be maintained by techniques including, but not limited to, applying higher levels of vacuum, higher pressures and/or levels of force to the aqueous solution and/or an applied gas pressure.

According to one embodiment of the invention, a substantial portion of the aqueous solution of amphiphilic macromolecules (e.g., amphiphilic proteins) may be drawn through the sheet in less than about 1 or 2 seconds to generate the appropriate shear stress conditions for adsorption. For example, a substantial portion of the aqueous solution may be drawn through the permeable sheet in less than about 0.1 second. As a further example, a substantial portion of the aqueous solution may be drawn through the permeable sheet in less than about 0.01 second. As yet another example, a substantial portion of the aqueous solution may be drawn through the permeable sheet in less than about 0.001 second. It is thought that appropriate shear stress conditions for adsorption of amphiphilic macromolecules (e.g., amphiphilic proteins) may be encountered when the flow of aqueous solution has a Reynold's number of at least about 200. For example, the flow of aqueous solution may have a Reynold's number of at least about 400.

In an important aspect of the invention, the material adsorbed on the individual exposed surfaces of the permeable sheet are amphiphilic macromolecues. Desirably, the amphiphilic macromolecues contain discretely separated hydrophilic and hydrophobic regions. Such amphiphilic macromolecules include, but are not limited to, synthetic polymers such as ionomers with separated areas of ionicity in an otherwise hydrophobic polymer, multiblock copolymers where every other block is highly charged or polar with the intervening blocks uncharged or nonpolar, protein, fatty acids, mucins, and other biological macromolecules with separated areas of hydrophilicity and hydrophobicity.

In another aspect of the present invention, the amphiphilic macromolecules are amphiphilic proteins. Generally speaking, the amphiphilic proteins may be selected from classes of globular proteins and/or random coil proteins. For example, the amphiphilic proteins may be milk proteins. Desirably, the amphiphilic proteins may include proteins such as those found in bovine milk including, for example, various caseins and whey proteins.

Milk proteins (e.g., bovine milk proteins) have been identified as well-suited to provide a durable surface modification when applied to a permeable substrate as describe above. The proteins in milk can be described as generally amphiphilic (i.e., they have both hydrophilic and hydrophobic regions) and tend to be surface active. Beta-casein (β-casein), one of the major milk proteins, is so surface active that it is used as an emulsifier in various food products. Other milk proteins include, but are not limited to, β-lactoglobulins and whey proteins.

EXAMPLES

SAMPLE PREPARATION

Experiments were conducted with four different types of surface-modified permeable cover materials. The four cover materials were: 1) milk protein treated polypropylene nonwoven web of meltblown fibers; 2) beta-casein treated polypropylene nonwoven web of meltblown fibers; 3) siloxane-polyether treated polypropylene nonwoven web of meltblown fibers; and 4) TRITON X-102 treated polypropylene nonwoven web of meltblown fibers.

Siloxane-polyether treated samples were used to assess the performance of a durable chemical surfactant treatment. TRITON-treated samples were used as control and represent conventional "fugitive" surfactant treatments.

Milk-Protein Treated Nonwoven Webs

Nonfat milk solutions of about 2.5 percent, by weight, nonfat milk were prepared by adding 25 g of Carnation® Natural Nonfat Dry Milk (Nestle Food Company) solids to 1000 g of distilled water and heating to approximately 70 degrees Centigrade. The resulting solution was stirred for 30 minutes and stored at 4 degrees Centigrade.

Solutions were generally allowed to equilibrate before being applied to permeable sheets of polypropylene nonwoven webs of meltblown fibers having a basis weight of about 1.5 osy (~51 gsm) available from Kimberly-Clark Corporation, Roswell, Ga. Protein deposition was achieved by placing an 18.5 cm diameter disk of the nonwoven web in a large Buchner funnel apparatus and applying vacuum under the sample so that application of 500 mL of the 2.5 percent, by weight, nonfat milk solution covered the entire surface of the nonwoven web. The nonfat milk solution initially wet the nonwoven web within one second and required an additional ten seconds to pass the entire volume of solution through the nonwoven web.

The nonwoven web was washed with 500 mL of distilled water while a vacuum was applied. The nonwoven web was allowed to dry at ambient temperature and the dry add-on of nonfat milk was measured to be approximately 0.38 percent, by weight.

Beta-Casein Treated Nonwoven Webs

Polypropylene nonwoven webs of meltblown fibers (basis weight of about 1.5 osy or ~51 gsm) were treated with beta-casein in accordance with the procedure described above. Deposition of beta-casein was accomplished using 200 mL of a 0.5 percent, by weight, aqueous solution of beta-casein. Like the nonfat milk solutions, the beta-casein solutions also initially wet the polypropylene nonwoven webs of meltblown fibers within one second. One sample was rinsed with water as above while the other was left unrinsed to test the role of the treatment's permanence in blood wicking and fluid surface tension reduction. The dry add-on of beta-casein for the rinsed samples were measured to be approximately 0.10 percent, by weight.

Durable Surfactant Treated Nonwoven Web

Polypropylene nonwoven webs of meltblown fibers (basis weight of about 1.5 osy (~5l gsm) with a durable surfactant treatment (siloxane polyether) were prepared by vacuum extraction with a water rinse generally in accordance with the procedure described above. Deposition of siloxane polyether was accomplished using 400 mL of 0.2 percent, by weight, aqueous solution of siloxane polyether TEGOPREN® 5830 (Goldschmidt Chemical Company, Hopewell, Va). The dry add-on of durable surfactant was measured to be approximately 0.36 percent, by weight.

Fugitive Surfactant Treated Nonwoven Web

Polypropylene nonwoven webs of meltblown fibers (basis weight of about 1.5 osy (~51 gsm) with a surfactant treatment (an octylphenoxypolyethoxyethanol nonionic surfactant, available under the trade designation "TRITON X-102" from Union Carbide Corporation, Danbury, Conn.) were prepared by soaking 7 inch by 10 inch samples of the nonwoven web for 2 minutes in 500 mL of an aqueous solution of 0.125 percent, by weight, of TRITON X-102. The soaked samples were nipped in an Atlas Laboratory Wringer (at 30 pounds pressure) and hung under a fume hood to dry at ambient conditions. The dry add-on of fugitive surfactant was measured to be approximately 0.65 percent, by weight. It should be noted that vacuum extraction treatment for the TRITON X-102 samples was not used because the surfactant's lack of durability on the polypropylene substrate would likely cause it to be washed away during sample preparation.

SAMPLE CHARACTERIZATION

Protein Deposition

X-ray Photoelectron Spectroscopy

X-ray Photoelectron Spectroscopy (XPS) data were collected using a Surface Science Labs M-Probe ESCA with monochromatic aluminum Kα radiation. All samples were mounted on double-side adhesive tape and charge neutralized with a 0.5 eV electron flood. Binding energies were referenced to C(1s) for hydrocarbon at 284.6 eV for charge compensation. XPS-detectable nitrogen was monitored to determine the nature of the coating and also to monitor the dependence of protein deposition on concentration, shear, and solvent washes.

Scanning Electron Microscopy

Field emission scanning electron microscopy analyses were carried out using a Hitachi S4500 field emission scanning electron microscope.

Staining/Optical Microscopy

For polarized light microscopy, samples were stained with ninhydrin spray reagent (0.2% ninhydrin in ethanol, Sigma Chemical Company) and dried at 55° C. until a definite purple color developed on controls. Samples were then observed with transmitted polarized light using a Zeiss polarized light microscope. Some samples were stained with Alizarin Red S (Aldrich Chemical Company, Inc.) by soaking treated samples in approximately 25 mL of 200 ppm alizarin in aqueous solution until a red color developed. These samples were rinsed with water and ambiently dried.

For fluorescence optical microscopy, samples were treated with protein-specific fluorescamine spray reagent (0.05% fluorescamine in acetone, Sigma Chemical Company) and immediately treated with 25 percent, by weight, ammonia (spray) to increase fluorescence intensity. After drying ambiently, the samples were observed using a Leitz Fluovert inverted microscope with excitation by long wavelength UV light (355–425 nm).

Coating Durability

The durability of the protein coatings was tested by exposing coated samples of the meltblown polypropylene web to various liquids/solutions and conditions intended to remove the coatings.

Solutions described below were passed through individual milk-protein treated meltblown polypropylene webs having a diameter of about 25 mm. Individual samples were held in a syringe disk filter and rinsed with one of the following:

20 mL distilled water, 10 mL 5 percent, by weight, acetic acid, 10 mL 0.5 M HCl, 10 mL 300 ppm TRITON X-102.

Samples were then rinsed with distilled water and dried at ambient conditions.

In addition, individual milk-protein treated meltblown polypropylene web samples having a diameter of about 25 mm were treated by 10 minutes of sonication in ethanol or boiling in 10 mL 1 percent, by weight, sodium dodecyl sulfate. Samples were then rinsed with distilled water and dried at ambient conditions.

XPS was used to determine the presence of protein on the surface of the meltblown polypropylene web samples.

Wettability and Surface Energy

Contact Angle Measurements

Contact angles of sessile drops of whole and nonfat milk solutions on a polypropylene film were determined using a Rame-Hart, Inc. goniometer (model number 100-00 115) equipped with a videocamera.

Fluid Surface Tension Reduction

Meltblown polypropylene webs having a basis weight of 1.5 osy (51 gsm) available from Kimberly-Clark Corporation were milk-protein treated. Samples measuring approximately 2"×3" were soaked for 24 hours in 80 mL of deionized water. The surface tension of the water was measured before and after sample soaking via the DuNouy ring method to determine if wetting of the material occurred via fluid surface tension reduction or by some other mechanism.

Critical Surface Tension of Wetting Measurements

Approximations of the critical surface tension of wetting of the milk-protein-treated materials were made by testing water wettability and by using wetting tension fluids available from Pillar Technologies, Inc. of Hartland, Wis. Sessile drops of the wetting fluids were placed on milk-protein-modified meltblown polypropylene webs in order of decreasing surface tension. The surface tension of the first drop to spread on the surface of the treated web within 2 seconds yielded an approximation of the treated web's critical surface tension of wetting in dynes/cm (which may be correlated to an approximation of surface energy). See, Bennet, M. K. and Zisman, W. A.; *Relation of Wettability by Aqueous Solutions to the Surface Constitution of Low Energy Solids*; J. Phys. Chem., pps. 1241–1246, Volume 63 (1959). The surface tensions of the fluids used in this analysis ranged from 50 to 70 dynes/cm. This analysis did not spatially resolve any coating anisotropy in the x, y-direction (patterning).

Blood wicking studies

Blood wicking performance of polypropylene nonwoven webs of meltblown fibers having various applied surface treatments was measured using the procedure described below. Fresh bovine blood was used in all studies. The hematocrit of initial investigations was not measured, but that of subsequent investigations was corrected to 30 percent.

Samples of polypropylene nonwoven webs of meltblown fibers (basis weight of approximately 1.5 osy (~51 gsm) were cut to dimensions of 3 inches by 7.5 inches, with the length aligned with the machine-direction of the nonwoven web. The samples were placed over a Kotex® Maxi pad (available from Kimberly-Clark corporation) that was modified by removing the conventional pad cover material. The modified pad and the experimental cover were each weighed separately. The pad and cover were placed on a colostomy bag (mounted on a lab jack) and were raised to contact a sheet of Plexiglas in order to adjust the applied pressure to 0.3 psi. Bovine blood was passed through an 18 gauge (1/32" diameter) orifice in the Plexiglas directly above the cover at a rate of 4 mL/hour (controlled by an infusion pump) . The stain dimensions were recorded periodically throughout the experiment. At the completion of the experiment, photographs and weights of the cover and pad were obtained.

EXPERIMENTAL RESULTS

Confirmation Of Protein Deposition

Figure 1:
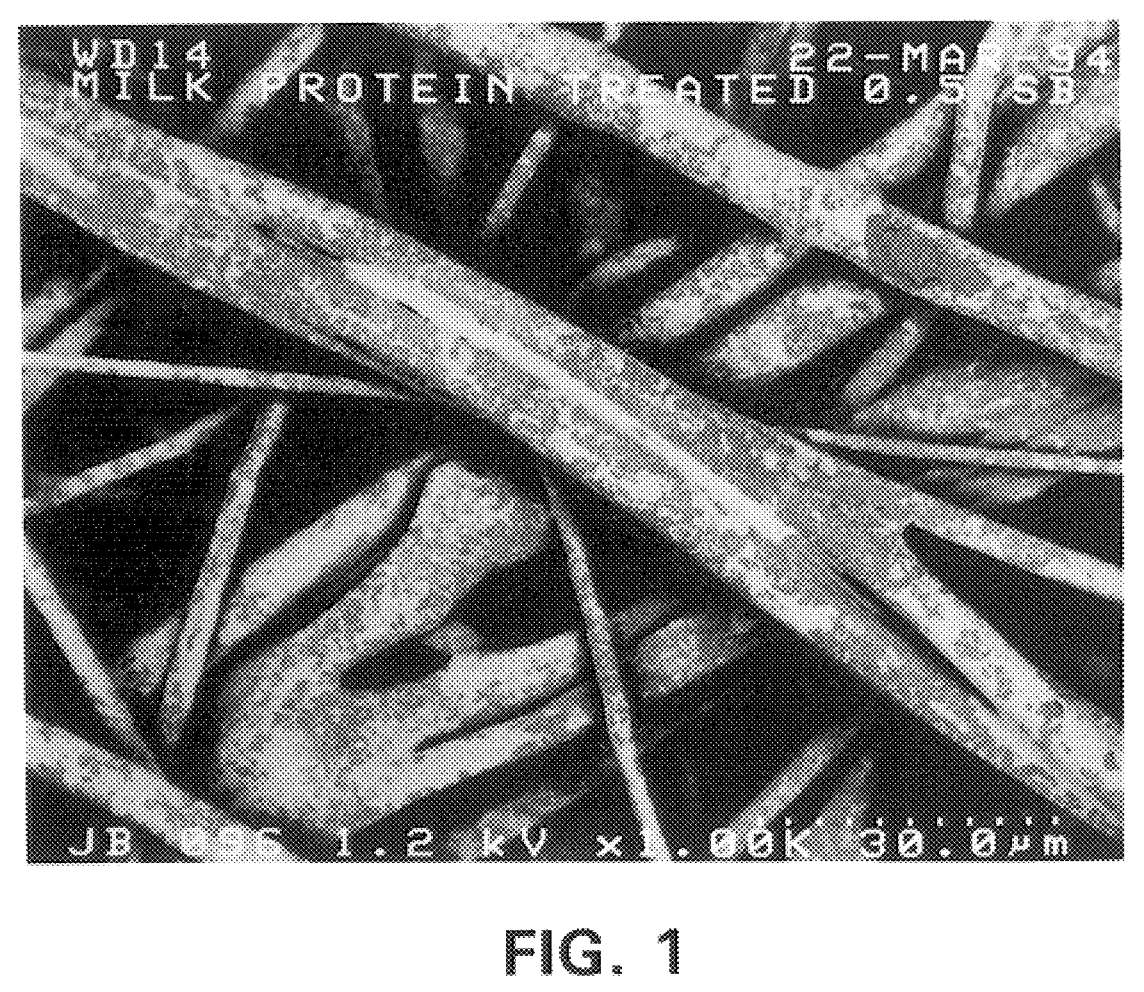

Milk protein modification of the meltblown fiber surface of the nonwoven polypropylene web was confirmed using fluorescence optical microscopy and XPS analyses. Fluorescence optical microscopy and scanning electron microscopy (SEM) indicated a coating which lies on the individual fibers of the nonwoven web and is not entrained in fiber intersections. XPS-detectable nitrogen values of the milk-protein treated surfaces ranged from 5–12% as summarized in Table 1. The uniformity of protein coating for the milk protein-treated polypropylene meltblown nonwoven web (exposed to protein in a non-homogenous shear field using the Buchner funnel procedure described above) was assessed by measuring XPS nitrogen intensity systematically at various spots on the nonwoven web surface. The results tabulated in Table 2 show the spot-to-spot agreement, suggesting a relatively uniform presence of a protein coating on the nonwoven web surface. FESEM micrographs (FIG. 1) corroborate these data, indicating a thin, tenacious coating which is relatively uniform along individual fibers and is not aggregated at fiber intersections. Apparent heterogeneity in the coating thickness in the FESEM micrograph is believed to result from differences in protein thickness and not from the presence of unmodified polypropylene.

However, when these coatings are stained (ninhydrin and Alizarin Red S) in bulk and observed macroscopically, a polka dot pattern is evident over the surface of the filter, as shown in FIG. 2. The polka dot pattern shown after staining corresponds to the holes in the Buchner funnel used in the vacuum deposition of the milk proteins. The holes in the funnel produce areas of high shear stress.

The agreement obtained for various analysis areas (XPS) over the surface of the milk-protein-treated samples suggests complete surface coverage, but bulk staining (ninhydrin) of the samples indicates a non-homogeneous coating, showing a polka-dot pattern of deposition which corresponds to the holes in the Buchner funnel used during the deposition. Taken together, the XPS results suggesting complete surface coverage and the bulk staining results indicating a non-homogeneous coating, suggest the surface of the nonwoven web is protein covered with isolated regions of greater deposition resulting from the shear dependence of the protein deposition and which cause patterned staining (and wettability, as discussed below).

Durable And Zoned Surface Treatment

Figure 3:
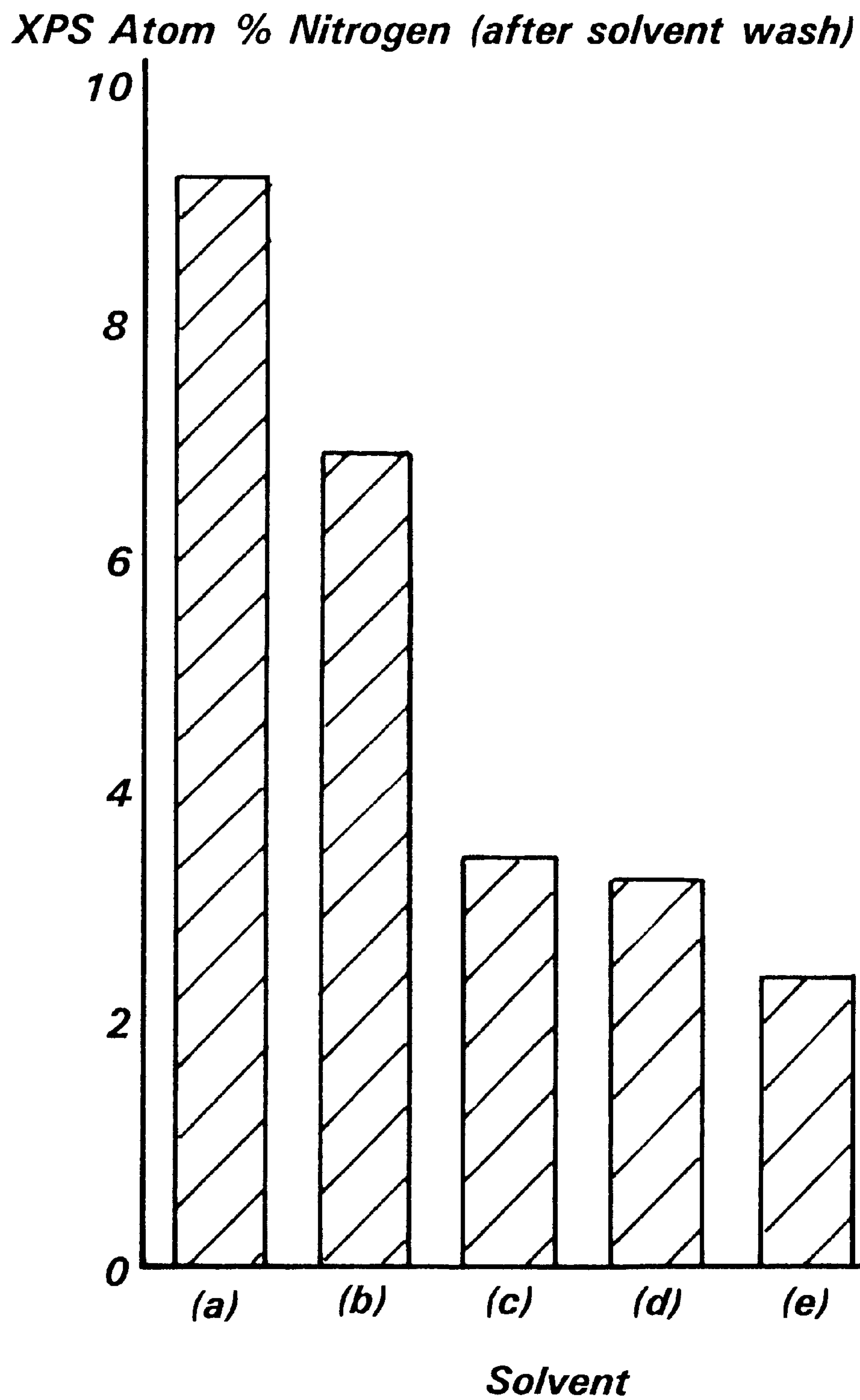
FIG. 3 is a representation of exemplary solvent durability of protein coatings on a permeable sheet.

Durability of the milk protein modification was tested against several solvents. The only method attempted which reliably removed the milk proteins from the polypropylene surface was 10 minutes exposure to boiling 1 percent, by weight, sodium dodecyl sulfate solution. The solvents used were (a) water; (b) ethanol; (c) 300 ppm TRITON X-102 solution; (d) 0.5 M HCl; (e) 5 percent, by weight acetic acid; and (f) 1 percent, by weight, sodium dodecyl sulfate solution. The results are summarized in FIG. 3.

Milk protein-treated nonwoven polypropylene webs of meltblown fibers were not instantly wettable by water or blood. However, they did wet within 5–10 seconds with a critical surface tension of wetting of approximately 60 dynes/cm. As summarized in Table 4, vacuum extraction of nonfat milk or β-casein solutions through the nonwoven web (followed by copious water rinsing) result in a material which was slowly wettable to water without a significant decrease in the water surface tension. This stands in contrast to traditional surfactant-treated materials which showed a decrease in the "final" water surface tension. That result suggests the milk-protein treatment method results in wettability by raising the apparent surface free energy of the material and not by reducing the surface tension of the wetting fluid. This wettability was observed to occur only in isolated regions of the protein treated substrate (i.e., in the polka-dot pattern corresponding to the holes in the Buchner funnel and observed via ninhydrin staining).

Figure 4:
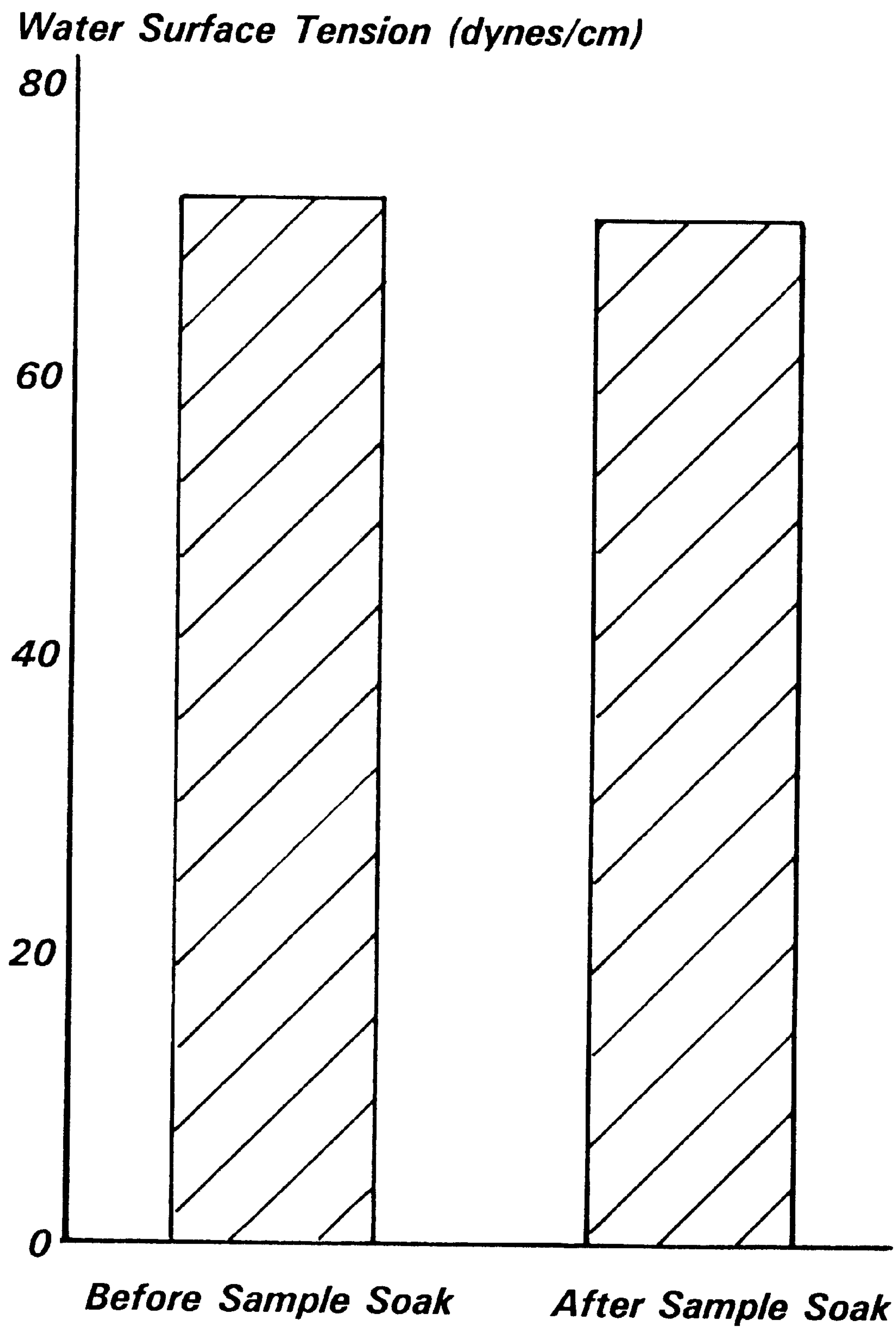
FIG. 4 is a representation of the effects of soaking an exemplary protein-coated permeable sheet on the fluid surface tension of the soaking solution.

In addition, milk protein treated nonwoven polypropylene webs of meltblown fibers were soaked in 80 mL deionized water for 24 hours to determine if any surface tension reduction could be measured for the wash solution. As shown in FIG. 4, the surface tension of the water prior to and after sample soaking was measured at 72 dynes/cm, indicating the absence of any β-casein at a concentration of greater than about 5 ppm in the solution after washing.

In comparison, the unrinsed β-casein-treated sample lowered the water surface tension by nearly 13 dynes/cm and was uniformly wetted by soaking in water. It is likely that the excess protein left in the nonwoven web (not rinsed away during preparation) dissolved in the wetting fluid and promoted uniform wetting, similar to the behavior observed for traditional surfactant treatments. Investigations of the wettability of the nonwoven web samples treated by vacuum extraction of a durable surfactant (siloxane polyether TEGOPREN® 5830) also demonstrated uniform wetting of the treated material.

Coupled with the XPS results which indicate the protein coating's substantiveness to water wash, these results stongly suggest that water wettability can be attributed to an increase in the surface free energy of the meltblown polypropylene nonwoven web instead of a decrease in the surface tension of the wetting fluid, characteristic of a durable protein coating. The wettability also occurs in the polka dot pattern observed during staining, which may be favorable in the control of fluid flow in absorbent structures and most likely results from the shear dependence of milk protein deposition.

Sided Surface Treatment

A sidedness or gradient distribution to the deposition can be observed, especially on higher basis weight nonwoven webs. A gradient distribution of protein coating is defined as that condition when the collective concentration of protein on individual exposed surfaces (e.g., individual fiber surfaces) within one length element of the permeable sheet (e.g., nonwoven fabric) is different than the collective protein concentration on an equal number of individual exposed surfaces (e.g., individual fiber surfaces) contained in an adjacent, equally sized element. The gradient distribution may be expressed by the following equation:

$$d[P]/d[t]\neq 0$$

Where P is the total protein concentration and t is the length element over which the protein concentration is measured. The total protein concentration (P) can be measured in the two orthogonal directions parallel to the surface or in the thickness direction (i.e., X, Y or Z gradients) For a matrix of fibrous material, the dimensions of t are on the order of integral multiples of fiber diameters. For example, t can be five fiber diameters. If the fibrous material is meltblown fibers, t is approximately 25 microns.

Differences in the XPS-detectable nitrogen between the top and bottom of milk-protein treated samples indicate this sidedness, as do measurements of the apparent surface free energies of all milk-protein treated materials as shown in Table 1.

As another example, a 18.5 cm diameter disk of 1.5 osy polypropylene meltblown nonwoven web (thickness 35 microns) was contacted with 1200 mL of a 2.5 percent, by weight, milk protein solution followed by a rinse with 600 mL of distilled water.

Table 3 summarizes data showing a gradient distribution or sidedness as indicated by differences in XPS-detectable nitrogen and surface free energies (e.g., 11% and 60 dynes/cm (top) vs. 6% and 50 dynes/cm (bottom)). Untreated meltblown polypropylene nonwoven web has a surface energy of about 36 dynes/cm and no XPS detectable nitrogen (i.e., <0.2 atom %). Analysis shows that the concentration of protein on the surface of the fibers is higher on the top side relative to the bottom. A top to bottom gradient is established. The apparent surface energy, determined by the maximum solution surface tension to wet the fabric, is higher on the top surface. This difference in apparent surface energy is manifest in a greater extent of water wettability for the top surface, and most likely results from the higher surface concentration of protein.

Additionally, the top side and the bottom side of the treated meltblown polypropylene nonwoven web was stained with Alizarin Red S. The top side exhibited high optical density and the bottom side exhibited low optical density. Because only the protein coating reacts with the red stain, the darker color (i.e., high optical density) further corroborates the presence of more protein on the top surface of the nonwoven web.

Taken together, these results strongly suggest that regions of greater protein deposition exist on the nonwoven substrate and these regions correspond to the pattern in the vacuum extraction "box" that was placed under the nonwoven substrate. The data also show a gradient of protein deposition through the polyolefin web which is manifest as a sidedness.

This sidedness was not observed for samples treated by vacuum extraction of a durable surfactant (siloxane polyether TEGOPREN® 5830) as shown in Table 1.

Results Of Controlled Wettability-Blood Wicking Studies

Figure 5A:
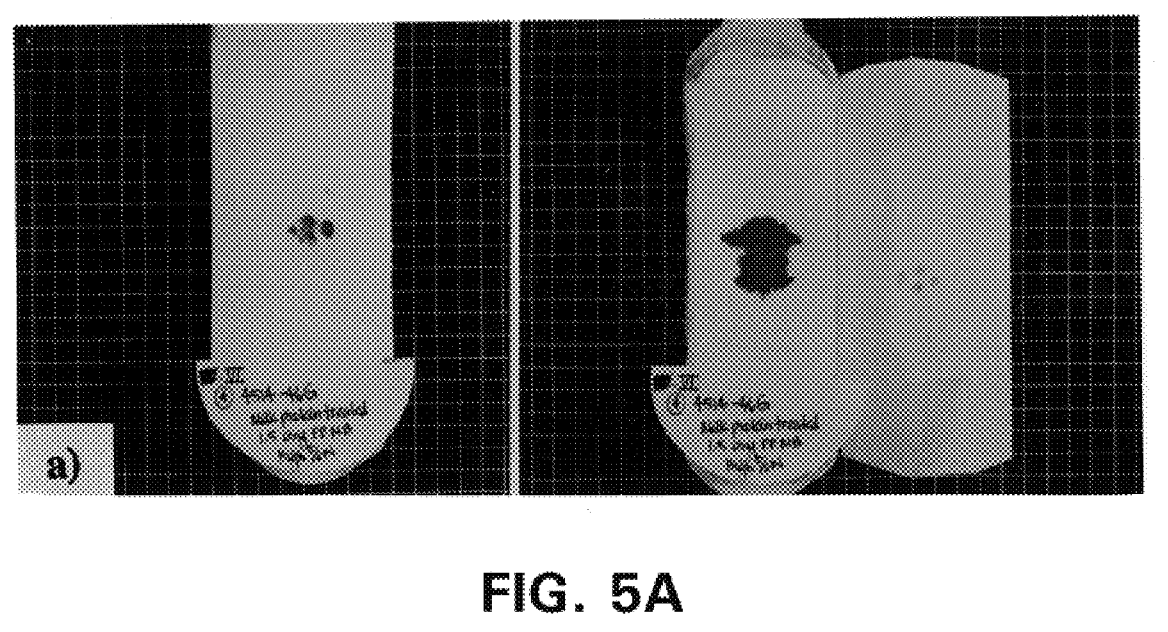
Figure 5B:
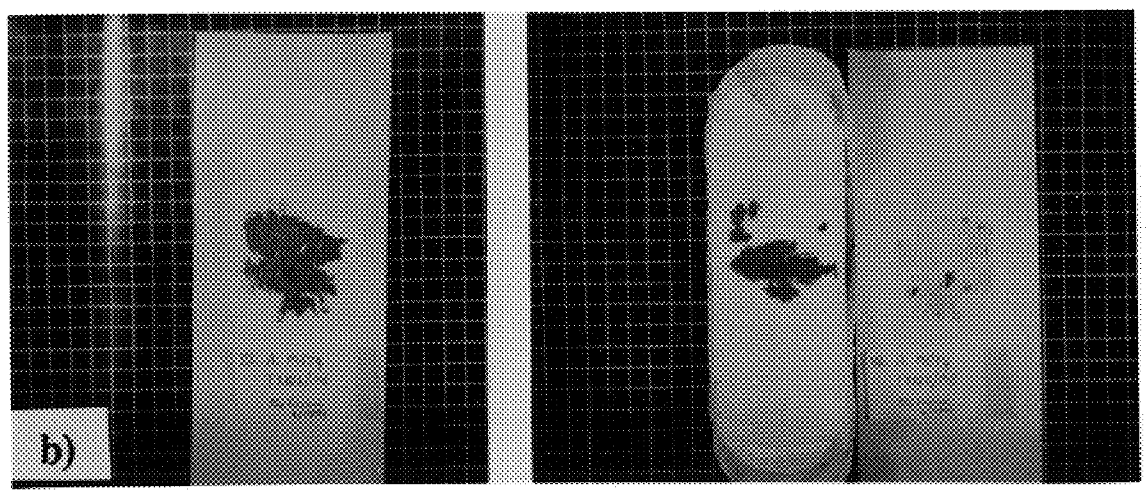

The spatially-controlled wettability imparted to nonwoven webs of meltblown polypropylene fibers treated by vacuum extraction of protein solutions appears to have direct consequences on the transfer of blood through a nonwoven web as illustrated in FIGS. 5A and 5B and Table 5.

FIG. 5A is a composite of two photographs (not to scale) of the absorbent pad with a milk-protein treated bodyside, permeable cover. The left side of FIG. 5A shows the cover surface, while the right side of the FIG. 5A shows the surface of the absorbent pad (which was located underneath the cover) as well as the backside of the cover. It should be noted that results shown in FIG. 5A were produced with the cover material oriented so that the side of the cover material exhibiting the higher critical surface tension of wetting was on the upper, top, or bodyside location. Blood wicking time was 45 minutes. As clearly seen in FIG. 5A, there is a lack of blood on the surface of the cover. Most of the blood is in the absorbent material underneath the cover.

The milk-protein treated cover shown in FIG. 5A exhibited some initial delay to blood wetting, which resulted in initial blood puddling (1.25 cm×2.25 cm, all stain sizes are given as machine direction 'MD'×cross-machine direction 'CD'). This initial stain did not increase in size during the experiment, but other spots arose from rewet of the cover from the absorbent underneath. Total blood retention in the cover (relative to the total amount of blood in pad and cover) was 0.4 percent, by weight. Deposition of milk proteins on the polypropylene nonwoven web via vacuum extraction has clearly improved the transfer of blood away from the surface of the nonwoven web (used as a permeable, bodyside cover material) resulting in less surface staining and blood retention. Although the inventors should not be held to a particular theory of operation, the favorable blood transfer characteristics of the milk-protein-treated nonwoven web of meltblown polypropylene fibers are believed to result from the spatially-controlled wettability of the treated material imparted by the gradient or graduated coating of protein on the low surface energy polypropylene substrate.

FIG. 5B is a composite of two photographs (not to scale) of the absorbent pad with the TRITON X-102 treated bodyside, permeable cover. The left side of FIG. 5B shows the cover surface, while the right side of the FIG. 5B shows the surface of the absorbent pad (which was located underneath the cover) as well as the backside of the cover. The TRITON X-102 treated cover was thought to have generally the same level of wettability on each side so that orientation of the cover was not considered significant factor affecting the ability of blood to pass through the thickness (Z-direction) of the cover. Blood wicking time was approximately 31 minutes.

In comparison to the milk-protein treated cover (FIG. 5A), the TRITON X-102-treated cover (FIG. 5B) developed an immediate stain which resulted from spreading of blood on the cover surface with a stain dimension of 5.1 cm×4.4 cm and total blood retention in the cover of 3.6 percent, by weight.

Another experiment was conducted utilizing a sample of the 1.5 osy (~51 gsm) nonwoven web of polypropylene meltblown fibers with no surface modification treatment of any kind as the bodyside cover material for an absorbent pad as described above. No photographs of the results of this experiment are shown. The untreated polypropylene cover material exhibited no blood wettability at all, even under an applied pressure of 0.3 psi. The blood spread over the surface of the nonwoven web and off of the pad, with negligible blood retention and transfer. Orientation of the web did not affect the spreading of the blood in the x,y-direction during these experiments.

Figure 6A:
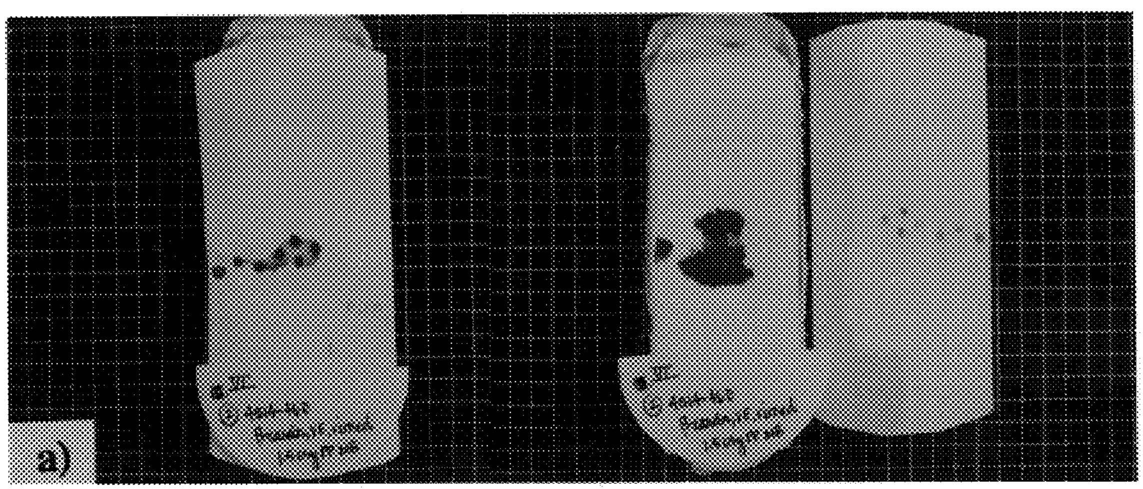
FIGS. 6A and 6B are photographs of an absorbent personal care product and permeable cover material.
Figure 6B:
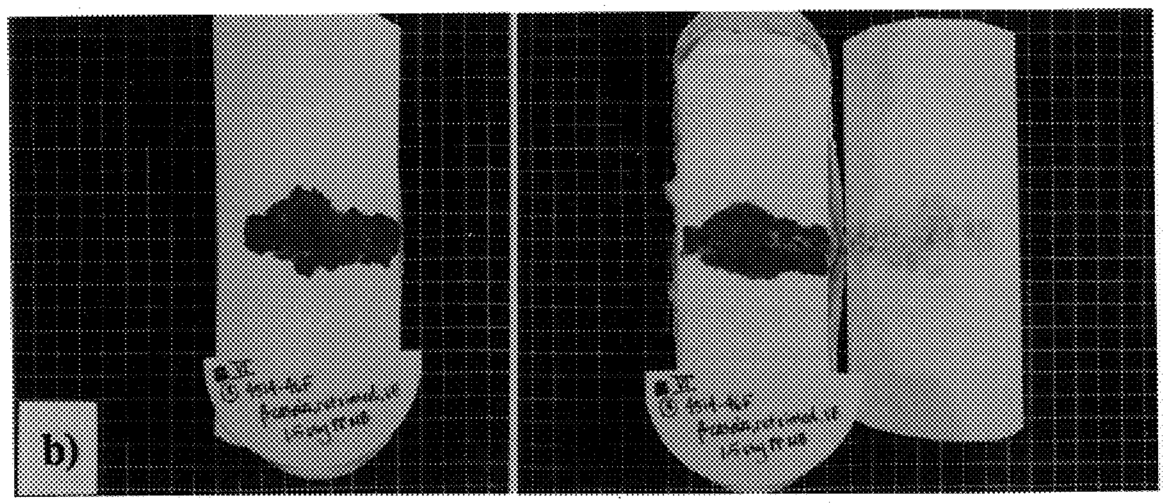

Samples with and without fugitive protein present were investigated in the blood wicking studies. Results of these studies are shown in FIGS. 6A and 6B. FIG. 6A is a composite of two photographs (not to scale) of the absorbent pad with a beta-casein treated bodyside, permeable cover. The left side of FIG. 6A shows the cover surface, while the right side of the FIG. 6A shows the surface of the absorbent pad (which was located underneath the cover) as well as the backside of the cover. FIG. 6B shows the same types of photographs for an unrinsed β-casein treated sample. It should be noted that results shown in FIGS. 6A and 6B were produced with the cover material oriented so that the side of the cover material exhibiting the higher critical surface tension of wetting was on the upper, top, or bodyside location. Blood wicking time for results shown in each of FIGS. 6A and 6B was 45 minutes.

The β-casein treated cover material shown in FIG. 6A was prepared via vacuum extraction and rinsed to remove excess protein. As can be seen from FIG. 6A, the cover yielded results very similar to those obtained for the similarly prepared milk-protein-treated sample, with a small initial stain (1.5 cm×5.25 cm) which did not spread over the course of the experiment and total blood retention in the cover of 0.8 percent, by weight. The initial spread of the stain along the width of the pad was caused by a delay in wetting of the cover by the initial blood insult. Once the cover was wetted, there was no additional spreading on the cover surface.

As can be seen in FIG. 6B (and by comparison to FIG. 5B), the unrinsed β-casein sample exhibited properties remarkably like those of TRITON X-102. The stain spread on the cover surface during the course of the experiment and had final dimensions of 3.75 cm×7.0 cm. Total blood retention in the cover was 6.1 percent, by weight. This similarity to TRITON X102 treated samples likely resulted from the fugitivity of excess protein in the nonwoven web causing fluid surface tension reduction and allowing spreading.

These blood wicking results are qualitatively very similar to the water wettability results given above and indicate that the combination of zoned and durable wettability, rather than just simple protein modification, renders the lateral spreading of blood unfavorable and results in better z-direction transfer of blood into the absorbent core underneath.

Figure 7A:
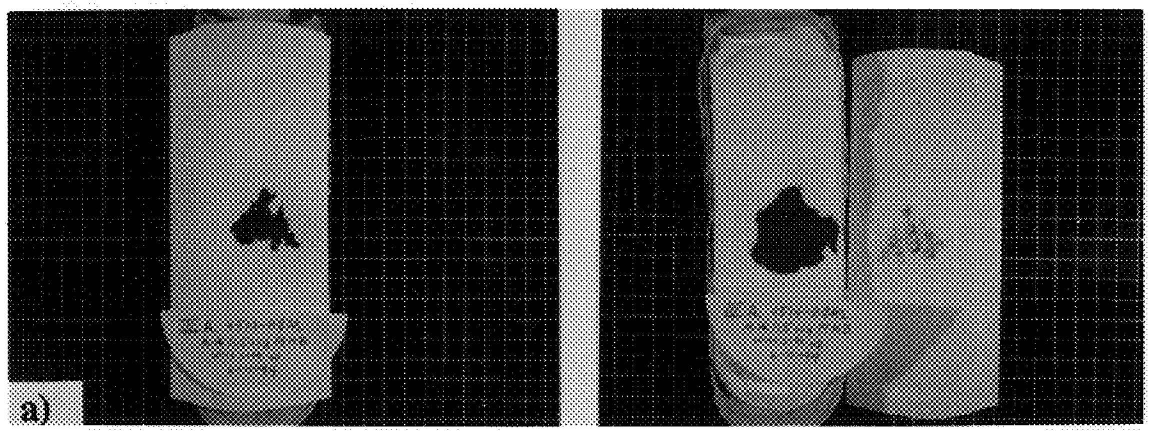
FIGS. 7A and 7B are photographs of an absorbent personal care product and permeable cover material.
Figure 7B:
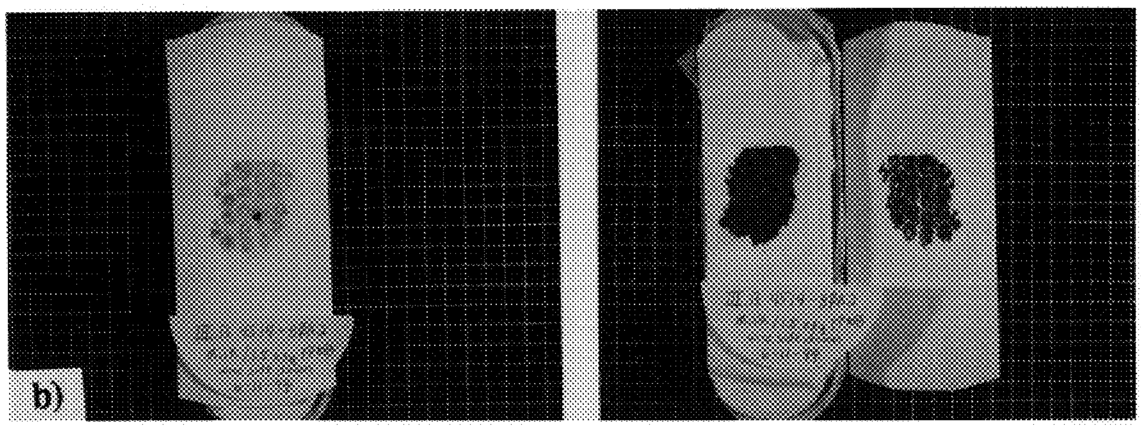

This z-directional transfer can also be assisted by the sidedness imparted to the treated material by vacuum extraction of milk proteins, as illustrated in FIGS. 7A and 7B. The left sides of both figures show the cover surface, while the right sides of both figures show the surface of the absorbent pad (which was located underneath the cover) as well as the backside of the cover. FIG. 7A is a composite of two photographs (not to scale) of the absorbent pad with a milk-protein treated bodyside, permeable cover. Results shown in FIG. 7A were produced with the cover material oriented so that the side of the cover material exhibiting the higher critical surface tension of wetting was on the upper, top, or bodyside location. Results shown in FIG. 7B were produced with the cover material oriented so that the side of the cover material exhibiting the lower critical surface tension of wetting was on the upper, top, or bodyside location. Blood wicking time for results shown in each of FIGS. 7A and 7B was 45 minutes.

As can be seen in FIG. 7A, a stain caused by initial puddling of the blood occurred on the side of the sample exhibiting the higher critical surface tension of wetting (which was oriented upward). The stain caused by this puddling did not increase in size over the course of the experiment and had a final dimension of 2.5 cm×3.25 cm, with total blood retention in the cover of 1.9 percent, by weight.

In comparison, the sample in FIG. 7B was placed so that the side of the sample exhibiting the lower critical surface tension of wetting was positioned upward. In this case, the stain observed resulted entirely from rewet of the cover from the absorbent underneath. Only a minuscule (2 mm×2 mm) stain occurred on the cover surface from the initial blood contact. The stain caused by rewet of the cover resembled a polka-dot pattern and was 4.5 cm×4.0 cm in size with total blood retention in the cover of 4.8 percent, by weight.

ESCA data and critical surface tension of wetting results in Tables 1 and 3 strongly suggest that the protein coating exhibited sidedness on the polyolefin web. It is generally thought that a gradient distribution of protein deposition exists throughout the depth of the polyolefin web. This gradient distribution of protein deposition is also thought to provide a graduated level of wettability into the depth (i.e., Z-direction) of the polyolefin web.

Such an increasing level of wettability into the depth or Z-direction of a permeable, bodyside cover material for an absorbent personal care product appears to promote preferential flow toward the area of higher wettability and into the absorbent pad underneath, allowing for less surface pooling and staining (at least under forced flow conditions) Accordingly, the expression "controlled wettability" refers to an increasing level of wettability along at least one dimension of permeable material (which otherwise would have relatively low surface energy). This increasing level of wettability (i.e., "controlled wettability") along at least one dimension of the permeable material is thought to correspond to an increase in surface energy along this dimension of the permeable material, which is due to a graduated level of protein deposition. The present invention should not be limited only to a "graduated" level of protein distribution. It is contemplated that controlled distribution of protein deposition or amphiphilic macromolecule deposition along at least one dimension of the permeable sheet may be in the form of a linear gradient distribution, a "step-function" type distribution or the like.

The "controlled wettability" or preference for flow toward areas of higher wettability resulted in blood retention on the side of the cover material with a higher critical surface tension of wetting (See, for example, FIGS. 7A and 7B). This effect may be used to control stain location and appearance as well as fluid distribution.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

TABLE 1

Summary of XPS and Critical Surface Tension of Wetting Measurements

| | XPS atom % Nitrogen (±1%) | | CST, dynes/cm (±2 dynes/cm)[a] | |
|---|---|---|---|---|
| Sample | Top[b] | Bottom | Top[b] | Bottom |
| PP MB Control | None | None | 36 | 36 |
| Milk-protein treated | 7.0 | 4.9 | 60 | 50 |
| β-casein treated, rinsed | 8.4 | Not Measured | 60 | 42 |
| β-casein, not rinsed | 11.7 | Not Measured | 64 | 50 |
| TRITON X-102 treated | N/A | N/A | WW[c] | Not Measured |
| Siloxane polyether TEGOPREN ® 5830[d] | N/A | N/A | 40 | 38 |

[a]CST = Critical Surface Tension of Wetting. Values reported were observed for several spots over the entire treated PP surface; the measurements did not spatially resolve the presence of the polka-dot pattern observed in staining.
[b]The top of the sample refers to the side of the PP MB with initial contact with solutions. The bottom is the side in direct contact with the surface of the Buchner funnel. It is the top side of the sample which exhibits greater deposition and higher critical surface tensions of wetting.
[c]WW = water wettable
[d]Siloxane polyether results are reported here to demonstrate that there is not a sidedness to this durable surfactant's deposition. XPS detectable silicon was monitored (top and bottom) in this case and was 8.5 atom % and 8.3 atom %, respectively.

TABLE 2

Uniformity of Milk Protein Coating on Filter Surface

| Sample Position[a] | % Nitrogen | % Nitrogen/% Carbon |
|---|---|---|
| A | 11.3 | 0.15 |
| B | 11.4 | 0.15 |
| C | 11.3 | 0.15 |
| D | 10.8 | 0.14 |
| E | 10.5 | 0.14 |
| F | 10.5 | 0.14 |
| G | 11.4 | 0.17 |
| H | 11.6 | 0.16 |
| I | 10.4 | 0.14 |
| J | 11.7 | 0.16 |

[a]Sample positions across a 49-mm diameter, milk protein treated, 0.5 osy polypropylene meltblown (PP MB) filter. The analysis was performed on the top side of a second disk exposed to 50 mL 2.5 percent, by weight, nonfat milk solution. The second exposure was used to eliminate the contribution of any mechanically-trapped particles to XPS-detectable nitrogen. Only carbon, nitrogen, and oxygen were detected on the filter surface.

TABLE 3

Sidedness of Milk Protein Deposition on PP MB

| | XPS % Nitrogen | | XPS N/C Ratio | |
|---|---|---|---|---|
| Sample | Top | Bottom | Top | Bottom |
| 0.5 osy[a] | 11.1 | 5.7 | 0.15 | 0.07 |
| | 11.8 | 9.5 | 0.17 | 0.12 |
| 1.5 osy[b] | 11.0 | 6.0 | 0.15 | 0.07 |

[a]Milk protein treated PP MB was made by passing 50 mL of 2.5 percent, by weight, nonfat milk solution through a 49-mm diameter 0.5 osy PP MB disk, followed by a rinse with 200 mL distilled water.
[b]Milk protein treated PP MB was made by passing 1200 mL of 2.5 percent, by weight, solution through a 18.5-cm diameter 1.5 osy PP MB disk, followed by a rinse with 600 mL of distilled water. Surface energies of the 1.5 osy PP MB were 60 dynes/cm and 50 dynes/cm for the top and bottom, respectively.

TABLE 4

Wetting Fluid Surface Tension Reduction Studies[a]

| | Water Surface Tension, dynes/cm (±1 dyne/cm) | |
|---|---|---|
| Sample | Initial | Final |
| Milk-protein-treated | 72.6 | 71.3 |
| β-casein-treated, rinsed | 72.7 | 71.3 |
| β-casein-treated, unrinsed | 72.6 | 59.7 |

[a]Surface tension reduction measurements were made using the DuNouy ring method.

TABLE 5

Blood Transfer Properties of Treated Materials[a]

| Sample | Side Exposed to Blood[b] | % Total Blood Retained in Cover(±0.2%) |
|---|---|---|
| Milk-protein treated | Top[b] | 1.0 |
| Milk-protein treated | Bottom | 4.8 |
| β-casein-treated, rinsed | Top | 0.8 |
| β-casein-treated, unrinsed | Top | 6.1 |
| TRITON X-102-treated | Top | 3.6 |

[a]Blood wicking studies were carried out as described in the text. Blood wicking time for all samples shown was 45 minutes, with the exception of the TRITON X-102-treated sample, which had a blood wicking time of 30.7 minutes.
[b]The top of the sample is as described in Table One.

What is claimed is:

1. A permeable, liquid flow control material comprising:

a permeable sheet having a plurality of individual exposed surfaces, at least a portion of which have a surface energy of less than about 45 dynes/cm;

amphiphilic proteins adsorbed onto at least some individual exposed surfaces of the permeable sheet to define a gradient distribution of amphiphilic protein coating along at least one dimension of the permeable sheet, and wherein the adsorbed amphiphilic protein coating provides controlled wettability along at least one dimension of the permeable, liquid flow control material wherein the permeable, liquid flow control material has a liquid retention of less than about 5 percent, by weight.

2. The permeable, liquid flow control material of claim 1 wherein the amphiphilic proteins are adsorbed on the permeable sheet such that the control material is substantially free of fugitive amphiphilic proteins.

3. The permeable, liquid flow control material of claim 1 wherein the amphiphilic proteins are adsorbed onto at least some individual exposed surfaces thereby defining a patterned protein coating on the permeable sheet.

4. The permeable, liquid flow control material of claim 1 wherein the coating of amphiphilic proteins uniformly adsorbed onto individual exposed surfaces is present in only discrete portions of the sheet material.

5. The permeable, liquid flow control material of claim 1 wherein the amphiphilic proteins are selected from the group consisting of globular proteins and random coil proteins.

6. The permeable, liquid flow control material of claim 1 wherein the amphiphilic proteins are milk proteins selected from the group consisting of β-casein, β-lactoglobulin and whey proteins.

7. The permeable, liquid flow control material of claim 1 wherein the control material has a liquid retention of less than about 3.5 percent, by weight.

8. The permeable, liquid flow control material of claim 1 wherein the coated sheet has a critical surface tension of wetting greater than about 50 dynes per centimeter.

9. The permeable, liquid flow control material of claim 1 wherein the coated sheet has a critical surface tension of wetting greater than about 60 dynes per centimeter.

10. The permeable, liquid flow control material of claim 1, wherein the gradient distribution of amphiphilic protein coating is along at least two dimensions of the permeable sheet.

11. The permeable, liquid flow control material of claim 10, wherein the adsorbed amphiphilic protein coating provides controlled wettability along at least two dimensions of the permeable sheet.

12. The permeable, liquid flow control material of claim 1, wherein the permeable sheet is a matrix of fibrous material.

13. The permeable, liquid flow control material of claim 12, wherein the nonwoven fabrics are selected from nonwoven webs of meltblown fibers, nonwoven webs of continuous spunbond filaments and bonded carded webs.

14. The permeable, liquid flow control material of claim 12, wherein the nonwoven web of meltblown fibers further includes one or more secondary materials selected from the group consisting of textile fibers, wood pulp fibers, particulates and super-absorbent materials.

15. The permeable, liquid flow control material of claim 12, wherein at least a portion of the fibrous material is a bi-component material selected from bi-component fibers and bi-component filaments.

16. The permeable, liquid flow control material of claim 1, wherein the permeable sheet is an apertured, film-like material.

17. The permeable, liquid flow control material of claim 1, wherein the material is a liquid intake material.

18. The permeable, liquid flow control material of claim 1, wherein the material is a liquid distribution material.

19. The permeable, liquid flow control material of claim 1, wherein the material is a liquid retention material.

20. A permeable, bodyside cover material for absorbent personal care products, the cover material comprising:

a permeable sheet having a plurality of individual exposed surfaces, at least a portion of which have a surface energy of less than about 45 dynes/cm;

amphiphilic proteins adsorbed onto at least some individual exposed surfaces of the permeable sheet to define a gradient distribution of amphiphilic protein coating along at least one dimension of the permeable sheet, such that the cover material is substantially free of fugitive amphiphilic proteins, and wherein the adsorbed amphiphilic protein coating provides controlled wettability along at least one dimension of the cover material wherein the cover material has a liquid retention of less than about 3.5 percent, by weight.

21. The permeable, bodyside cover material of claim 20, wherein the gradient distribution of amphiphilic protein coating is along at least two dimensions of the permeable sheet.

22. The permeable, bodyside cover material of claim 21, wherein the adsorbed amphiphilic protein coating provides controlled wettability along at least two dimensions of the permeable sheet.

23. A permeable, liquid flow control material comprising:

a permeable sheet having a plurality of individual exposed surfaces, at least a portion of which have a surface energy of less than about 45 dynes/cm;

amphiphilic proteins adsorbed onto at least some individual exposed surfaces of the permeable sheet to define a gradient distribution of amphiphilic macromolecule coating along at least one dimension of the permeable sheet, such that the permeable, liquid flow control material is substantially free of fugitive amphiphilic macromolecules, and wherein the adsorbed amphiphilic macromolecule coating provides controlled wettability along at least one dimension of the permeable, liquid flow control material and wherein the permeable, liquid flow control material has a liquid retention of less than about 3.5 percent, by weight.

24. The permeable, liquid flow control material of claim 23, wherein the amphiphilic macromolecules are selected from ionomers with separated areas of ionicity in an otherwise hydrophobic polymer, multiblock copolymers where every other block is highly charged with the intervening blocks uncharged, amphiphilic proteins, fatty acids, mucins, and biological macromolecules with separated areas of hydrophilicity and hydrophobicity.

25. An absorbent article comprising:

a liquid permeable topsheet having a plurality of individual exposed surfaces, at least a portion of which having a surface energy of less than about 45 dyne/cm;

amphiphilic molecules adsorbed onto at least some individual exposed surfaces of the liquid permeable topsheet to define a gradient distribution of amphiphilic molecules coating along at least one dimension of the permeable sheet wherein the adsorbed amphiphilic molecule coating provides controlled wettability along at least one dimension of the liquid permeable topsheet and the liquid permeable topsheet has a liquid retention of less than about 3.5 percent, by weight;

a liquid impervious barrier sheet; and an absorbent core between the liquid permeable topsheet and the liquid impervious barrier sheet.

* * * * *